(12) United States Patent
Wybo et al.

(10) Patent No.: US 12,727,784 B2
(45) Date of Patent: Sep. 8, 2026

(54) WIRELESS NEUROMUSCULAR SENSING DEVICE

(71) Applicant: Depuy Synthes Products, Inc., Raynham, MA (US)

(72) Inventors: Christopher Wybo, Brighton, MI (US); Aashish Shah, Ann Arbor, MI (US); Tarik Yardibi, Reading, MA (US); Emir Osmanagic, Norwell, MA (US); Darren Scarfe, LaSalle (CA)

(73) Assignee: DePuy Synthes Products, Inc., Raynham, MA (US)

( * ) Notice: Subject to any disclaimer, the term of this patent is extended or adjusted under 35 U.S.C. 154(b) by 799 days.

(21) Appl. No.: 16/158,739

(22) Filed: Oct. 12, 2018

(65) Prior Publication Data

US 2020/0113485 A1 Apr. 16, 2020

(51) Int. Cl.

*A61B 5/11* (2006.01)
*A61B 5/00* (2006.01)
*A61B 5/05* (2021.01)

(52) U.S. Cl.

CPC ............... *A61B 5/1106* (2013.01); *A61B 5/05* (2013.01); *A61B 5/4519* (2013.01); *A61B 2505/05* (2013.01); *A61B 2562/0219* (2013.01)

(58) Field of Classification Search

CPC ....... A61B 5/1106; A61B 5/1107; A61B 5/30; A61B 5/389; A61B 5/395; A61B 5/4029;

(Continued)

(56) References Cited

U.S. PATENT DOCUMENTS 3,200,814 A 8/1965 Taylor et al.
3,565,080 A 2/1971 Ide et al.

(Continued)

FOREIGN PATENT DOCUMENTS

EP 1417000 A2 5/2004
EP 1575010 A1 9/2005

(Continued)

OTHER PUBLICATIONS

J. Herdmann MD; V. Deletis MD PHD; H.Edmonds PHD; N. Morota MD, Spinal Cord and Nerve Root Monitoring in Spine Surgery and Related Procedures, Spine Journal, Apr. 1, 1996, pp. 879-885, vol. 21.

(Continued)

*Primary Examiner* — Devin B Henson
(74) *Attorney, Agent, or Firm* — Condo Roccia Koptiw LLP

(57) ABSTRACT

A sensing device for detecting an artificially induced neuromuscular response within a limb of a subject includes a plurality of mechanical sensors, wireless communication circuitry, and a processor in electrical communication with each of the plurality of mechanical sensors and wireless communication circuitry. Each sensor is operative to monitor a mechanical response of a different muscle group of the limb and generate a mechanomyography (MMG) output signal corresponding to the monitored motion. The processor receives and buffers a portion of each MMG output signal, determines if the MMG output signal from any one or more of the plurality of mechanical sensors is representative of an artificially induced neuromuscular response, and transmits one or more of the buffered MMG output signals to a host system only if the output signal from one or more of the sensors is determined to be representative of an artificially induced neuromuscular response.

19 Claims, 6 Drawing Sheets

(58) Field of Classification Search
CPC ... A61B 5/4041; A61B 5/4519; A61B 5/4893; A61B 5/7221; A61B 5/7264; A61B 5/7278; A61B 5/7282; A61B 5/7296; A61B 2562/0219; A61B 2505/05
See application file for complete search history.

(56) References Cited

U.S. PATENT DOCUMENTS 3,797,010 A 3/1974 Adler et al.
4,155,353 A 5/1979 Rea et al.
4,493,327 A 1/1985 Bergelson et al.
4,807,642 A 2/1989 Brown
4,817,628 A 4/1989 Zealear et al.
4,940,453 A 7/1990 Cadwell
4,994,015 A 2/1991 Cadwell
5,047,005 A 9/1991 Cadwell
5,078,674 A 1/1992 Cadwell
5,116,304 A 5/1992 Cadwell
5,178,145 A 1/1993 Rea
5,284,153 A 2/1994 Raymond et al.
5,284,154 A 2/1994 Raymond et al.
5,482,038 A 1/1996 Ruff
5,566,678 A 10/1996 Cadwell
5,593,429 A 1/1997 Ruff
5,631,667 A 5/1997 Cadwell
5,775,331 A 7/1998 Raymond et al.
5,860,939 A 1/1999 Wofford et al.
5,888,370 A 3/1999 Becker et al.
5,993,630 A 11/1999 Becker et al.
5,993,632 A 11/1999 Becker et al.
6,030,401 A 2/2000 Marino
6,093,205 A 7/2000 McLeod et al.
6,181,961 B1 1/2001 Prass
6,183,518 B1 2/2001 Ross et al.
6,206,921 B1 3/2001 Guagliano et al.
6,221,082 B1 4/2001 Marino et al.
6,224,603 B1 5/2001 Marino
6,251,140 B1 6/2001 Marino et al.
6,264,659 B1 7/2001 Ross et al.
6,266,394 B1 7/2001 Marino
6,266,558 B1 7/2001 Gozani et al.
6,280,447 B1 8/2001 Marino et al.
6,287,832 B1 9/2001 Becker et al.
6,290,724 B1 9/2001 Marino
6,312,443 B1 11/2001 Stone
6,324,432 B1 11/2001 Rigaux et al.
6,361,508 B1 3/2002 Johnson et al.
6,368,325 B1 4/2002 McKinley et al.
6,387,070 B1 5/2002 Marino et al.
6,387,130 B1 5/2002 Stone et al.
6,436,143 B1 8/2002 Ross et al.
6,466,817 B1 10/2002 Kaula et al.
6,478,805 B1 11/2002 Marino et al.
6,485,518 B1 11/2002 Cornwall et al.
6,491,626 B1 12/2002 Stone et al.
6,500,128 B2 12/2002 Marino
6,519,319 B1 2/2003 Marino et al.
6,530,930 B1 3/2003 Marino et al.
6,533,797 B1 3/2003 Stone et al.
6,540,747 B1 4/2003 Marino
6,564,078 B1 5/2003 Marino et al.
6,638,281 B2 10/2003 Gorek
6,641,708 B1 11/2003 Becker et al.
6,654,634 B1 11/2003 Prass
6,739,112 B1 5/2004 Marino
6,760,616 B2 7/2004 Hoey et al.
6,764,452 B1 7/2004 Gillespie et al.
6,764,489 B2 7/2004 Ferree
6,802,844 B2 10/2004 Ferree
6,805,668 B1 10/2004 Cadwell
6,807,438 B1 10/2004 Brun Del Re et al.
6,843,790 B2 1/2005 Ferree
6,852,126 B2 2/2005 Ahlgren
6,870,109 B1 3/2005 Villarreal
6,887,248 B2 5/2005 McKinley et al.
6,923,814 B1 8/2005 Hildebrand et al.
6,945,973 B2 9/2005 Bray
6,964,674 B1 11/2005 Matsuura et al.
6,972,199 B2 12/2005 Lebouitz et al.
6,981,990 B2 1/2006 Keller
7,001,432 B2 2/2006 Keller et al.
7,025,769 B1 4/2006 Ferree
7,050,848 B2 5/2006 Hoey et al.
7,072,521 B1 7/2006 Cadwell
7,079,883 B2 7/2006 Marino et al.
7,160,303 B2 1/2007 Keller
7,162,850 B2 1/2007 Marino et al.
7,166,113 B2 1/2007 Arambula et al.
7,175,662 B2 2/2007 Link et al.
7,177,677 B2 2/2007 Kaula et al.
7,207,949 B2 4/2007 Miles et al.
7,214,197 B2 5/2007 Prass
7,214,225 B2 5/2007 Ellis et al.
7,216,001 B2 5/2007 Hacker et al.
7,230,688 B1 6/2007 Villarreal
7,236,832 B2 6/2007 Hemmerling et al.
7,267,691 B2 9/2007 Keller et al.
7,296,500 B1 11/2007 Martinelli
7,320,689 B2 1/2008 Keller
7,338,531 B2 3/2008 Ellis et al.
7,341,590 B2 3/2008 Ferree
7,367,958 B2 5/2008 McBean et al.
7,374,448 B2 5/2008 Jepsen et al.
7,379,767 B2 5/2008 Rea
7,470,236 B1 * 12/2008 Kelleher .......... A61B 17/00234
7,485,146 B1 2/2009 Crook et al.
7,522,953 B2 4/2009 Kaula et al.
7,527,629 B2 5/2009 Link et al.
7,527,649 B1 5/2009 Blain
7,553,307 B2 6/2009 Bleich et al.
7,555,343 B2 6/2009 Bleich
7,569,067 B2 8/2009 Keller
7,578,819 B2 8/2009 Bleich et al.
7,582,058 B1 9/2009 Miles et al.
7,583,991 B2 9/2009 Rea
7,611,522 B2 11/2009 Gorek
7,618,423 B1 11/2009 Valentine et al.
7,628,813 B2 12/2009 Link
7,634,315 B2 12/2009 Cholette
7,657,308 B2 2/2010 Miles et al.
7,664,544 B2 2/2010 Miles et al.
7,666,195 B2 2/2010 Kelleher et al.
7,668,588 B2 2/2010 Kovacs
7,691,057 B2 4/2010 Miles et al.
7,693,562 B2 4/2010 Marino et al.
7,708,776 B1 5/2010 Blain et al.
7,713,463 B1 5/2010 Reah et al.
7,722,613 B2 5/2010 Sutterlin et al.
7,722,673 B2 5/2010 Keller
7,738,968 B2 6/2010 Bleich
7,738,969 B2 6/2010 Bleich
7,740,631 B2 6/2010 Bleich et al.
7,766,816 B2 8/2010 Chin et al.
7,776,049 B1 8/2010 Curran et al.
7,776,094 B2 8/2010 McKinley et al.
7,785,248 B2 8/2010 Annest et al.
7,785,253 B1 8/2010 Arambula et al.
7,815,682 B1 10/2010 Peterson et al.
7,819,801 B2 10/2010 Miles et al.
7,828,855 B2 11/2010 Ellis et al.
7,833,251 B1 11/2010 Ahlgren et al.
7,857,813 B2 12/2010 Schmitz et al.
7,862,592 B2 1/2011 Peterson et al.
7,862,614 B2 1/2011 Keller et al.
7,867,277 B1 1/2011 Tohmeh
7,883,527 B2 2/2011 Matsuura et al.
7,887,538 B2 2/2011 Bleich et al.
7,887,568 B2 2/2011 Ahlgren
7,887,595 B1 2/2011 Pimenta
7,892,173 B2 2/2011 Miles et al.
7,901,430 B2 3/2011 Matsuura et al.
7,905,840 B2 3/2011 Pimenta et al.
7,905,886 B1 3/2011 Curran et al.
7,914,350 B1 3/2011 Bozich et al.

(56) References Cited

U.S. PATENT DOCUMENTS 7,918,849 B2 4/2011 Bleich et al.
7,918,891 B1 4/2011 Curran et al.
7,920,922 B2 4/2011 Gharib et al.
7,927,337 B2 4/2011 Keller
7,935,051 B2 5/2011 Miles et al.
7,938,830 B2 5/2011 Saadat et al.
7,942,104 B2 5/2011 Butcher et al.
7,942,826 B1 5/2011 Scholl et al.
7,946,236 B2 5/2011 Butcher
7,959,577 B2 6/2011 Schmitz et al.
7,962,191 B2 6/2011 Marino et al.
7,963,915 B2 6/2011 Bleich
7,963,927 B2 6/2011 Kelleher et al.
7,981,058 B2 7/2011 Akay
7,981,144 B2 7/2011 Geist et al.
7,991,463 B2 8/2011 Kelleher et al.
8,000,782 B2 8/2011 Gharib et al.
8,005,535 B2 8/2011 Gharib et al.
8,012,212 B2 9/2011 Link et al.
8,016,767 B2 9/2011 Miles et al.
8,016,776 B2 9/2011 Bourget et al.
8,027,716 B2 9/2011 Gharib et al.
8,031,075 B2 * 10/2011 Buchnick ........... G08B 21/0446 340/573.1
8,048,080 B2 11/2011 Bleich et al.
8,050,769 B2 11/2011 Gharib et al.
8,055,349 B2 11/2011 Gharib et al.
8,062,298 B2 11/2011 Schmitz et al.
8,062,300 B2 11/2011 Schmitz et al.
8,062,369 B2 11/2011 Link
8,062,370 B2 11/2011 Keller et al.
8,063,770 B2 11/2011 Costantino
8,068,912 B2 11/2011 Kaula et al.
8,070,812 B2 12/2011 Keller
8,074,591 B2 12/2011 Butcher et al.
8,075,499 B2 12/2011 Nathan et al.
8,075,601 B2 12/2011 Young
8,083,685 B2 12/2011 Fagin et al.
8,083,796 B1 12/2011 Raiszadeh et al.
8,088,163 B1 1/2012 Kleiner
8,088,164 B2 1/2012 Keller
8,090,436 B2 1/2012 Hoey et al.
8,092,455 B2 1/2012 Neubardt et al.
8,092,456 B2 1/2012 Bleich et al.
8,103,339 B2 1/2012 Rea
8,114,019 B2 2/2012 Miles et al.
8,114,162 B1 2/2012 Bradley
8,123,668 B2 2/2012 Annest et al.
8,133,173 B2 3/2012 Miles et al.
8,137,284 B2 3/2012 Miles et al.
8,147,421 B2 4/2012 Farquhar et al.
8,147,551 B2 4/2012 Link et al.
8,165,653 B2 4/2012 Marino et al.
8,167,915 B2 5/2012 Ferree et al.
8,172,750 B2 5/2012 Miles et al.
8,206,312 B2 6/2012 Farquhar
8,255,044 B2 8/2012 Miles et al.
8,255,045 B2 8/2012 Gharib et al.
8,303,515 B2 11/2012 Miles et al.
8,337,410 B2 12/2012 Kelleher et al.
8,343,065 B2 1/2013 Bartol et al.
8,343,079 B2 1/2013 Bartol et al.
8,394,129 B2 3/2013 Morgenstern Lopez et al.
8,500,653 B2 8/2013 Farquhar
8,500,738 B2 8/2013 Wolf, II
8,517,954 B2 8/2013 Bartol et al.
8,535,224 B2 9/2013 Cusimano Reaston et al.
8,538,539 B2 9/2013 Gharib et al.
8,556,808 B2 10/2013 Miles et al.
8,562,539 B2 10/2013 Marino
8,562,660 B2 10/2013 Peyman
8,568,317 B1 10/2013 Gharib et al.
8,591,431 B2 11/2013 Calancie et al.
8,641,638 B2 2/2014 Kelleher et al.
8,731,654 B2 5/2014 Johnson et al.
8,784,330 B1 7/2014 Scholl et al.
8,792,977 B2 7/2014 Kakei et al.
8,855,822 B2 10/2014 Bartol et al.
8,864,654 B2 10/2014 Kleiner et al.
8,936,626 B1 1/2015 Tohmeh et al.
8,945,004 B2 2/2015 Miles et al.
8,958,869 B2 2/2015 Kelleher et al.
8,982,593 B2 3/2015 Nondahl et al.
8,989,855 B2 3/2015 Murphy et al.
8,989,866 B2 3/2015 Gharib et al.
9,014,776 B2 4/2015 Marino et al.
9,014,797 B2 4/2015 Shiffman et al.
9,037,250 B2 5/2015 Kaula et al.
9,066,701 B1 6/2015 Finley et al.
9,084,550 B1 * 7/2015 Bartol .................. A61B 5/4893
9,084,551 B2 7/2015 Brunnett et al.
9,131,947 B2 9/2015 Ferree
9,192,415 B1 11/2015 Arnold et al.
9,295,396 B2 3/2016 Gharib et al.
9,295,401 B2 3/2016 Cadwell
9,301,711 B2 4/2016 Bartol et al.
9,392,953 B1 7/2016 Gharib
9,446,259 B2 9/2016 Phillips et al.
10,004,406 B2 6/2018 Yuen et al.
10,130,298 B2 * 11/2018 Mokaya ............... A61B 5/0024
2001/0031916 A1 10/2001 Bennett et al.
2002/0038092 A1 3/2002 Stanaland et al.
2002/0165590 A1 11/2002 Crowe et al.
2003/0074037 A1 4/2003 Moore et al.
2004/0077969 A1 4/2004 Onda et al.
2004/0082877 A1 4/2004 Kouou et al.
2004/0186535 A1 9/2004 Knowlton
2004/0230138 A1 11/2004 Inoue et al.
2004/0243018 A1 12/2004 Organ et al.
2005/0075578 A1 4/2005 Gharib et al.
2005/0085741 A1 4/2005 Hoskonen et al.
2005/0102007 A1 5/2005 Ayal et al.
2005/0240086 A1 10/2005 Akay
2005/0245839 A1 11/2005 Stivoric et al.
2005/0280531 A1 12/2005 Fadem et al.
2005/0283204 A1 12/2005 Buhlmann et al.
2006/0020177 A1 1/2006 Seo et al.
2006/0052726 A1 3/2006 Weisz et al.
2006/0135888 A1 6/2006 Mimnagh-Kelleher et al.
2006/0270949 A1 11/2006 Mathie et al.
2007/0038155 A1 2/2007 Kelly et al.
2007/0049826 A1 3/2007 Willis
2007/0232958 A1 10/2007 Donofrio et al.
2007/0265675 A1 11/2007 Lund et al.
2007/0276270 A1 11/2007 Tran
2008/0051643 A1 2/2008 Park et al.
2008/0058656 A1 3/2008 Costello et al.
2008/0076978 A1 3/2008 Ouchi et al.
2008/0167695 A1 7/2008 Tehrani et al.
2008/0234767 A1 9/2008 Salmon et al.
2008/0306363 A1 12/2008 Chaiken et al.
2008/0306397 A1 12/2008 Bonmassar et al.
2008/0312560 A1 12/2008 Jamsen et al.
2008/0312709 A1 12/2008 Volpe et al.
2009/0036747 A1 2/2009 Hayter et al.
2009/0062696 A1 3/2009 Nathan et al.
2009/0069709 A1 3/2009 Schmitz et al.
2009/0069722 A1 3/2009 Flaction et al.
2009/0076336 A1 3/2009 Mazar et al.
2009/0171381 A1 7/2009 Schmitz et al.
2009/0192413 A1 7/2009 Sela et al.
2009/0228068 A1 9/2009 Buhlmann et al.
2009/0247910 A1 10/2009 Klapper
2009/0306741 A1 12/2009 Hogle et al.
2009/0318779 A1 12/2009 Tran
2010/0090834 A1 4/2010 Buchnick et al.
2010/0137748 A1 6/2010 Sone et al.
2010/0152619 A1 6/2010 Kalpaxis et al.
2010/0152622 A1 6/2010 Teulings
2010/0152623 A1 6/2010 Williams
2010/0168559 A1 7/2010 Tegg et al.
2010/0262042 A1 10/2010 Kirn
2010/0292617 A1 11/2010 Lei et al.
2011/0004207 A1 1/2011 Wallace et al.

(56) References Cited

U.S. PATENT DOCUMENTS

| | | | | |
|---|---|---|---|---|
| 2011/0230782 | A1 | 9/2011 | Bartol et al. | |
| 2011/0237974 | A1 | 9/2011 | Bartol et al. | |
| 2011/0270121 | A1 | 11/2011 | Johnson et al. | |
| 2011/0301665 | A1 | 12/2011 | Mercanzini et al. | |
| 2012/0053491 | A1 | 3/2012 | Nathan et al. | |
| 2012/0157886 | A1* | 6/2012 | Tenn | A61B 5/389 600/595 |
| 2012/0191003 | A1 | 7/2012 | Garabedian et al. | |
| 2013/0197321 | A1 | 8/2013 | Wilson | |
| 2013/0204097 | A1 | 8/2013 | Rondoni et al. | |
| 2013/0213659 | A1 | 8/2013 | Luyster et al. | |
| 2013/0253533 | A1 | 9/2013 | Bartol et al. | |
| 2014/0020178 | A1 | 1/2014 | Stashuk et al. | |
| 2014/0066803 | A1 | 3/2014 | Choi | |
| 2014/0088029 | A1 | 3/2014 | Sugimoto et al. | |
| 2014/0121555 | A1 | 5/2014 | Scott et al. | |
| 2014/0148725 | A1 | 5/2014 | Cadwell | |
| 2014/0163411 | A1 | 6/2014 | Rea | |
| 2014/0275926 | A1 | 9/2014 | Scott et al. | |
| 2014/0276195 | A1 | 9/2014 | Papay et al. | |
| 2014/0358026 | A1 | 12/2014 | Mashiach et al. | |
| 2015/0032022 | A1 | 1/2015 | Stone et al. | |
| 2015/0045699 | A1 | 2/2015 | Mokaya et al. | |
| 2015/0045783 | A1 | 2/2015 | Edidin | |
| 2015/0051470 | A1* | 2/2015 | Bailey | A61B 5/681 600/300 |
| 2015/0051506 | A1 | 2/2015 | Wybo et al. | |
| 2015/0054654 | A1* | 2/2015 | Albinali | G08B 21/02 340/870.01 |
| 2015/0112325 | A1 | 4/2015 | Whitman | |
| 2015/0157227 | A1 | 6/2015 | Kelleher et al. | |
| 2015/0230749 | A1 | 8/2015 | Gharib et al. | |
| 2015/0342521 | A1 | 12/2015 | Narita et al. | |
| 2015/0342621 | A1 | 12/2015 | Jackson, III | |
| 2016/0051812 | A1 | 2/2016 | Montgomery, Jr. et al. | |
| 2020/0069943 | A1* | 3/2020 | Campean | A61N 1/36021 |

FOREIGN PATENT DOCUMENTS

| | | | |
|---|---|---|---|
| EP | 2231003 | A1 | 9/2010 |
| EP | 2535082 | A1 | 12/2012 |
| EP | 3110166 | A1 | 12/2016 |
| FR | 2920087 | A1 | 2/2009 |
| JP | 2008073456 | A | 4/2008 |
| JP | 2018054617 | A | 4/2018 |
| JP | 2018138127 | A | 9/2018 |
| WO | 0078209 | A2 | 12/2000 |
| WO | 2007024147 | A1 | 3/2007 |
| WO | 2014160832 | A2 | 10/2014 |
| WO | 2015171619 | A1 | 11/2015 |
| WO | 2016100340 | A1 | 6/2016 |
| WO | 2017156718 | A1 | 9/2017 |
| WO | 2018065971 | A1 | 4/2018 |

OTHER PUBLICATIONS

N. Hollands MB, BS; J. Kostuik. Continuous Electromyographic Moniotring to Detect Nerve Root Injury During Thoracolumbar Scoliosis Surgery, Spine Journal, Nov. 1, 1997, pp. 2547-2550, vol. 22, Issue 21.

C. Harper, J. Daube, Facial Nerve Electromyography and Other Cranial Nerve Monitoring, Journal of Clinical Neurophysiology, May 1998, pp. 206-216, vol. 15, Issue 3.

D. Beck, J. Ben Ecke Jr, Intraoperative Facial Nerve Monitoring Technical Aspects, Official Journal of the American Academy of Otolaryngology—Head and Neck Surgery Foundation, Apr. 27, 1989.

W. Welch MD, R. Rose PHD, J. Balzer PHD, G. Jacobs, MD, Evaluation with evoked and spontaneous electromyography during lumbar instrumentation: a prospective study, Journal of Neurosurgery, Sep. 1997, pp. 397-402, vol. 87, No. 3.

W. Young MD, D. Morledge PHD, W. Martin PHD, K. Park MD, Intraoperative Stimulation of Pedicle Screws: A New Method for Verification of Screw Placement, Journal of Neurosurgery, 1995, pp. 544-547 vol. 44.

K. Sugita MD, S. Kobayashi MD, Technical and instrumental improvements in the surgical treatment of acoustic neurinomas, Journal of Neurosurgery, Dec. 1982, pp. 747-752, vol. 57.

J. Boston, L. Deneault, Sensory evoked potentials: a system for clinical testing and patient monitoring, International Journal of Clinical Monitoring and Computing, 1984, pp. 13-19, Martinus Nijhoff Publishers, Netherlands.

A. Moller, Neuromonitoring in Operations in the Skull Base, The Keio Journal of Medicine, Oct. 1991, pp. 151-159.

J. Maurer, H. Pelster, W. Mann, Intraoperatives Monitoring motorischer Hurnnerven bei Operationen an Hals und Schadelbasis, Laryngo-Rhino-Otol, pp. 561-567, vol. 73.

W. Friedman MD, M. Curran R. EPT, Somatosensory Evoked Potentials after Sequential Extremity Stimulation: A New Method for Improved Monitoring Accuracy, Neurosurgery, 1987, pp. 755-758, vol. 21, No. 5.

R. Gopalan, P. Parker, R. Scott, Microprocessor-Based System for Monitoring Spinal Evoked Potentials During Surgery, IEEE Transactions on Biomedical Engineering, Oct. 1986, pp. 982-985, vol. BME-22, No. 10.

B. Moed MD, B. Ahmad MD, J. Craig MD, G. Jacobson PHD, M. Anders MD, Intraoperative Monitoring with Stimulus-Evoked Electromyography during Placement Iliosacral Screws, The Journal of Bone and Joint Surgery, Apr. 1998, pp. 537-546, vol. 80-A, No. 4, The Journal of Bone and Joint Surgery, Inc.

C. Yingling PHD, J. Gardi PHD, Intraoperative Monitoring of Facial and Cochlear Nerves During Acoustic Neuroma Surgery, Acoustic Neuroma I, Apr. 1992, pp. 413-448, vol. 25, No. 2, Otolaryngologic Clinics of North America.

N. Holland MB, BS, J. Kostuik MD, Continuous Electromyographic Monitoring to Detect Nerve Root Injury During Thoracolumbar Scoliosis Surgery, Spine, 1997, pp. 2547-2550, vol. 22, No. 21, Lippincott-Raven Publishers.

P. Dulguerov, F. Marchal, W. Lehmann, Postparotidectomy Facial Nerve Paralysis: Possible Etiologic Factors and Results with Routine Facial Nerve Monitoring, The Laryngoscope, May 1999, pp. 754-762 vol. 109, Lippincott Williams & Wilkins, Inc. Philadelphia, Pennsylvania.

M. Imai MS, Y. Harada MD, Y. Atsuta MD, Y. Takemitsu MD, T. Iwahara MD, Automated Spinal Cord Monitoring for Spinal Surgery, Paraplegia, 1989, pp. 204-211.

R. Witt, Facial nerve monitoring in parotid surgery: The standard of care?, Otolaryngology—Head and Neck Surgery, Nov. 1998, pp. 468-470, vol. 119, No. 5.

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

(56) References Cited

OTHER PUBLICATIONS

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.
Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.
Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.
Yuhao, et al. "Intraoperative monitoring of neuromuscular function with soft, skin-mounted wireless devices" NPJ Digital Medicine, May 23, 2018 (May 23, 2018), pp. 1-10.
International search report for international application EP19202100.
Farina, D., et al., "High-Density EMG E-Textile Systems for the Control of Active Prostheses," 32nd Annual International Conference of the IEEE EMBS Buenos Aires, Argentina, Aug. 31-Sep. 4, 2010.
Braden, R. "Internet Engineering Task Force—Memo on Requirements for Internet Hosts—Communication Layers," Oct. 1989.
Querry, R.G., et al., "Synchronous stimulation and monitoring of soleus H reflex during robotic body weight-supported ambulation in subjects with spinal cord injury," Journal of Rehabilitation Research and Development, vol. 45, p. 175-186, Nov. 1, 2008.
International search report on international application EP19202100.4.

* cited by examiner

WIRELESS NEUROMUSCULAR SENSING DEVICE

TECHNICAL FIELD

The present disclosure relates generally to a surgical diagnostic system employing a wireless sensing device for detecting artificially induced neuromuscular activity.

BACKGROUND

Traditional surgical practices emphasize the importance of recognizing or verifying the location of nerves to avoid injuring them. Recent advances in surgical techniques include the development of techniques using ever smaller incisions, such as minimally invasive surgical procedures, and the insertion of ever more complex medical devices. With these advances in surgical techniques, there is a corresponding need for improvements in methods of detecting and/or avoiding nerves.

In many surgical procedures, it may be common to include ancillary monitoring devices or therapeutic devices provided around limbs or other anatomy of the subject. Each device may include wires or tubes that extend between the patient-contacting component and a separate monitoring/control station. These wires/tubes may create a congested area immediately surrounding the patient, which may potentially interfere with the surgical team's ability to move freely within the operating room.

Therefore, while the need for nerve detection/monitoring exists, the corresponding wiring that could extend from a purely wired implementation may further congest an already crowded operating suite.

SUMMARY

A sensing device for detecting an artificially induced neuromuscular response within a limb of a subject includes a plurality of mechanical sensors, wireless communication circuitry, and a processor in electrical communication with each of the plurality of mechanical sensors and wireless communication circuitry. Each sensor is operative to monitor a mechanical response of a different muscle group of the limb and generate a mechanomyography (MMG) output signal corresponding to the monitored motion. The processor receives and buffers a portion of each MMG output signal, determines if the MMG output signal from any one or more of the plurality of mechanical sensors is representative of an artificially induced neuromuscular response, and transmits one or more of the buffered MMG output signals to a host system only if the output signal from one or more of the sensors is determined to be representative of an artificially induced neuromuscular response.

A system for detecting the presence of a nerve within an intracorporeal treatment area of a subject includes a host system, a first sensing device and a second sensing device. The host system may include a display for outputting data and/or alerts to a surgical team.

The first sensing device may include a first plurality of mechanical sensors, each operative to monitor a mechanical response of a different muscle group of a first portion of the subject and each configured to generate a respective mechanomyography (MMG) output signal corresponding to the monitored motion. The first device further includes a first processor in communication with each mechanical sensor of the first plurality of mechanical sensors and configured to receive each of the generated MMG output signals from the first plurality of mechanical sensors.

The second sensing device may include a second plurality of mechanical sensors, each operative to monitor a mechanical response of a different muscle group of a second portion of the subject and each configured to generate a respective mechanomyography (MMG) output signal corresponding to the monitored motion. The second device further includes a second processor in communication with each mechanical sensor of the second plurality of mechanical sensors and configured to receive each of the generated MMG output signals from the first plurality of mechanical sensors.

To minimize the chance of wires interfering with the surgical procedures each of the first processor and second processor are in wireless digital communication with the host system and are each operative to wirelessly transmit at least a portion of one or more MMG output signals to the host system for output via the display.

The features and advantages and other features and advantages of the present technology are readily apparent from the following detailed description when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
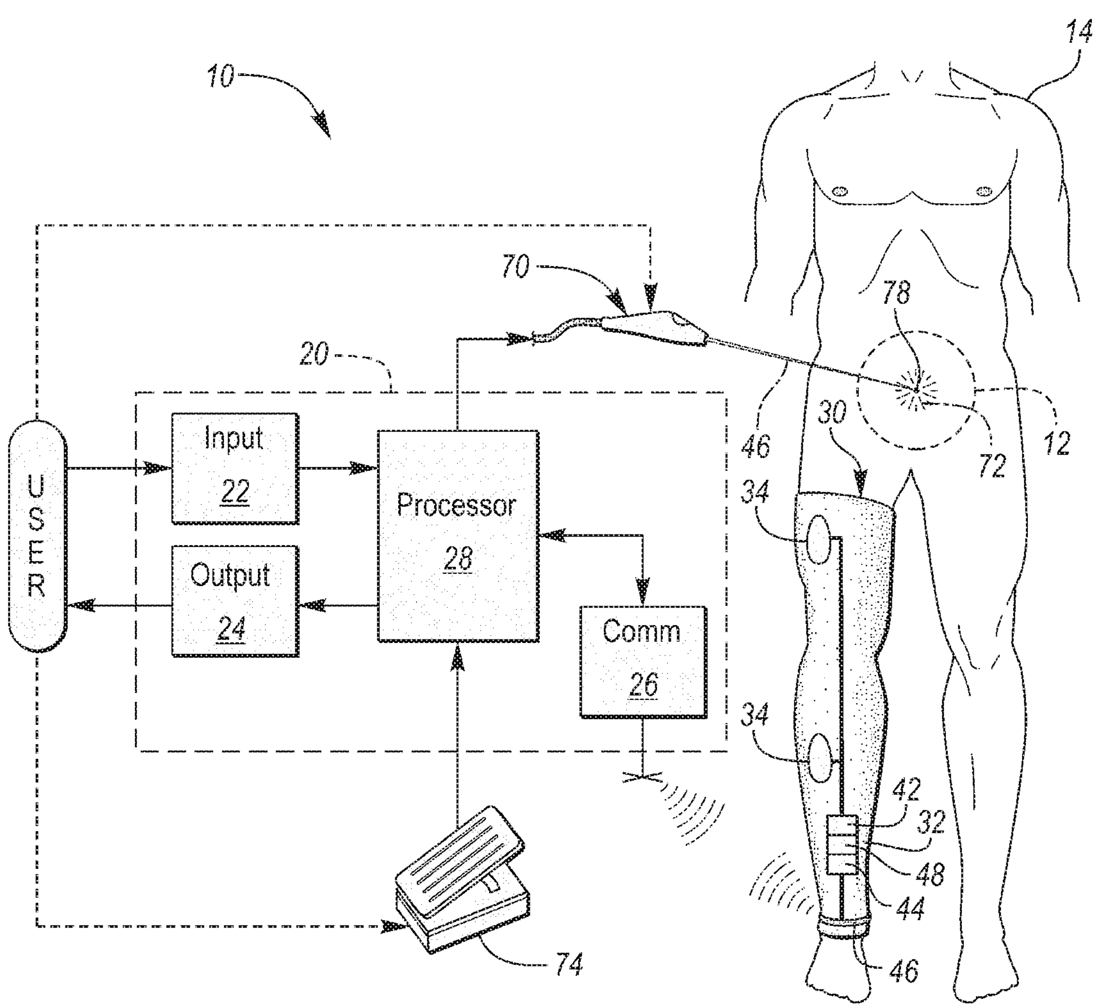
FIG. 1 is a schematic diagram of a neural monitoring system for detecting an artificially-induced mechanical muscle response.

The present disclosure provides a wireless sensing device for detecting an artificially induced neuromuscular response of a subject. The device may include an array of neuromuscular sensors that are locally monitored on the device and collectively networked with a separate host system via a wireless radio frequency (RF) communication circuitry.

The sensor array of the present device may be adapted to monitor a plurality of different muscle groups of the subject. Each neuromuscular sensor in the array may be held in contact with the skin of the subject immediately adjacent to each monitored muscle group. In most embodiments, each sensor in the array includes a mechanical sensor that is operative to monitor the mechanical motion of the adjacent muscle group and to generate an output signal corresponding to that sensed motion. Using various processing techniques, the system may then be capable of discerning whether the sensed mechanical motion is representative of an artificially induced muscle response.

While the individual output signals and signal data may be useful for identifying induced muscle responses and determining the proximity of a nerve to an invasive stimulator, unconstrained and continuous wireless data transmission incurs a significant power draw that may quickly deplete onboard power stores/batteries. As such, in certain embodiments, the sensing device may include a local processor that is capable of performing at least a preliminary analysis on the monitored responses and then transmitting only sensor data that likely represents an induced neuromuscular response. Alternatively, the local processor my downsample and/or reduce the resolution of any sensor data that is not representative of an induced neuromuscular response prior to transmission. Because induced responses tend to be sporadic and somewhat infrequent, this filtering technique greatly reduces that amount and frequency of data that must be transmitted and the corresponding power consumption of the onboard communications circuitry. This may permit a reduction in the size of a required battery and/or may increase the duration of device use on a single charge.

The present "filtering" technique serves to reduce the quantity and/or frequency of wireless data transmission by only transmitting full resolution data when an induced muscle response is likely to exist. In embodiments where data transmission only occurs when the processor detects something, periods of data transmission may be interpreted as being representative of an induced response, and periods of no transmission may be interpreted as being representative of a lack of an induced response (which is also significantly informative to a surgeon). Unfortunately, in such an embodiment, the lack of a response may also be caused by a drop in wireless connectivity, where even if a response were to exist, it would not be communicated. To address this concern, in some embodiments, a connection diagnostic data packet may be periodically communicated between the sensing device and the host system to provide an indication of the fidelity of the wireless communication link. In some embodiments, the connection diagnostic packet may be a checksum or other diagnostic packet that is transmitted back to the sensing device upon conclusion of a transmitted message. If the fidelity of the communication link drops or entirely falls out, as may be determined via the diagnostic packet, the system may provide an alert to indicate that the negative inference should not be trusted (i.e., the negative inference that no transmission=no induced response).

In some embodiments, the local processor may detect the likelihood of an induced muscle response by analyzing the sensor signals individually and/or in the collective. To perform this analysis, each signal may be locally buffered by the processor across a rolling period, and then the buffered signals may be analyzed to determine signal traits indicative of an induced response. Processing techniques that may be employed involve techniques to actively filter out noise, gross motion, and/or signal content outside of an expected response window, while also examining the signal or signals from the sensors for attributes or patterns that are indicative of an induced response.

To minimize pre-operative setup while reducing the potential for error, the sensor device may be provided as an integrated unit that may be affixed to the subject by either securing it around the limb (similar to a blood pressure cuff) or by pulling the device onto the subject, such as with anti-embolism stockings. In doing so, the carrier material may locate the array about the subject in a quicker manner than if each sensor was individually placed.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14, such as during a surgical procedure. As will be described in greater detail below, the system 10 may monitor one or more muscles of the subject 14 for a neuromuscular response that is indicative of a stimulus-induced depolarization of a nerve (i.e., an artificially induced neuromuscular response). If a response of the muscle to the stimulus is detected during the procedure, the system 10 may provide an alert or indication to the surgeon, which may enable the surgeon to take an appropriate action if such action is warranted.

As used herein, an "artificially induced neuromuscular response" is a response of a muscle to a depolarizing stimulus that is applied to a nerve innervating the muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may artificially cause the nerve to depolarize (resulting in a corresponding contraction of the muscle or muscles innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially induced neuromuscular response, a muscle innervated by the artificially depolarized nerve may physically contract or relax (i.e., a mechanical response) and/or the electrical potential throughout the muscle may be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

The neural monitoring system 10 may generally include a host system 20 and a sensing device 30 that may cooperate to detect a neuromuscular response of a muscle to a stimulus 72 provided by a stimulator 70. As schematically shown in FIG. 1, the host system 20 may include one or more input devices 22 that are operative to receive information from the surgeon, one or more output devices 24 that are operative to communicate alerts or to provide informational feedback to the surgeon, communication circuitry 26 operative to communicate with the sensing device 30, and a processor 28 that is operative to at least manage the flow of information between the input devices 22, output devices 24 and communication circuitry 26.

In general, the one or more input devices 22 may include a keyboard, a mouse, and/or a digitizer provided with a touch-screen display. These devices may receive pre-operative case information or may permit a surgeon to alter various intraoperative parameters, alarm limits, or other case information before or during a procedure. In some embodiments, the stimulator 70 and/or a foot pedal 74 may provide additional input to the host system 20. This input may be in the form of an analog or digital signal that is indicative of the delivery and/or magnitude of a stimulus. The output device 24 may include, for example, a visual display such as an LED/LCD display, one or more indicator lights, or speakers capable of providing an audible alert to the surgeon.

The sensing device 30 is the portion of the system 10 that directly contacts the subject 14 and is responsible for, at a minimum, sensing/detecting neuromuscular responses of the subject 14. The sensing device 30 may include a carrier material 32 that is operative to be secured to the subject 14, and a plurality of neuromuscular sensors 34 (i.e., a sensor array) that are each operative to monitor a neuromuscular response of a different muscle group of the subject 14.

From the perspective of the sensing device 30, the carrier material's main purpose is to hold the neuromuscular sensors 34 in relatively stable contact with the skin of the subject. While the present technology has a beneficial use with electromyography (EMG) (i.e., by ensuring that needle electrodes are held in firm, relative position in the muscle without much risk of falling out), the full functionality and accuracy of the device 30 is best realized when the neuromuscular sensors 34 are configured to monitor the mechanical responses of the various muscles. As such, in an embodiment, at least a plurality of the neuromuscular sensors 34 include a mechanical sensor 36, such as for example, a strain gauge, a pressure/force transducer, a position encoder, an accelerometer, a piezoelectric material, or any other transducer or combination of transducers that may convert a physical motion into a variable electrical signal.

At a device-level, each of the plurality of neuromuscular sensors 34 may provide an output signal 38 that corresponds to or that is representative of its sensed level of neuromuscular activity. In some embodiments, each sensor 34 may include communication circuitry 40 to facilitate transmission of the output signal to a local device processor 42 (note that the communication circuitry 40 may be integral to the mechanical sensor 36, or may not be required depending on the architecture of the array). In effect, this collection of wired sensors to the local processor 42 may form a device-level, serial network that may be managed by the processor 42 or by a secondary component operating in conjunction with the processor 42.

Figure 2:
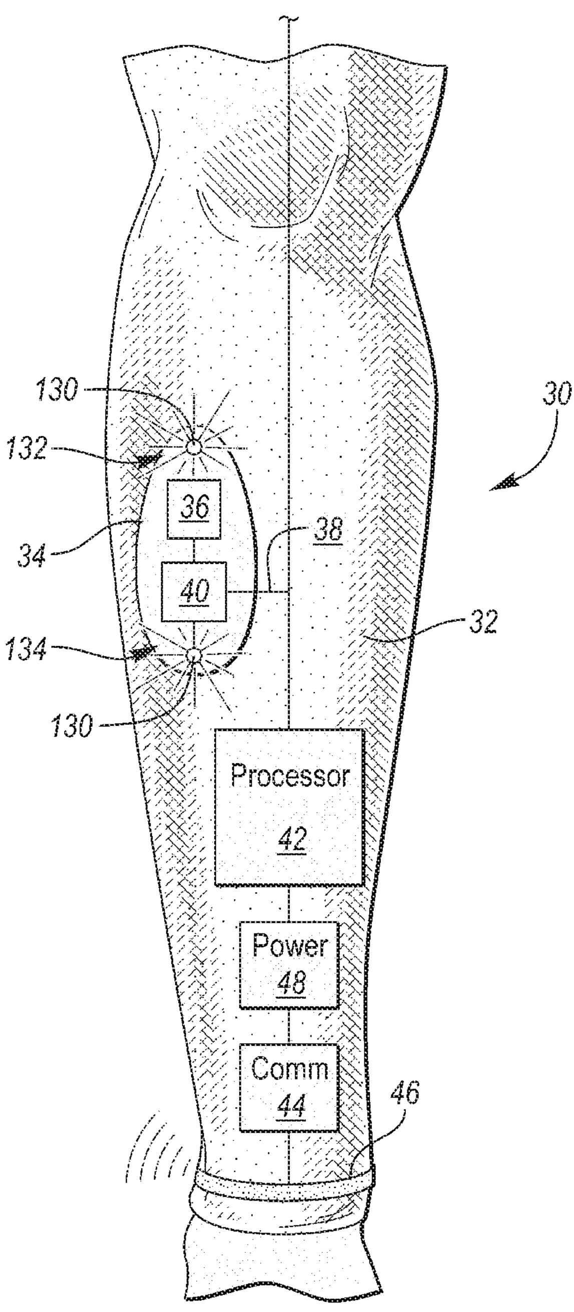
FIG. 2 is an enlarged schematic anterior view of a sensing device provided on a leg of a subject.

As schematically shown in FIG. 2, the sensing device 30 may include wireless communication circuitry 44 that is operative to digitally communicate with the communication circuitry 26 of the host system 20, an antenna 46, a power source 48, and the local processor 42 in communication with each of these. In general, processors used with the present system 10 (e.g., processors 28, 42) may each be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

In some embodiments, the power source 48 may comprise a wired power supply, such as an alternating-current line voltage. Such a design, however, negates some of the benefits of the wireless communications and wireless nature of the device, since wires extending from the sensing device 30 would still be required. Because an object of the present disclosure is to reduce or eliminate the need for wires extending from the sensing device 30, in a more preferred embodiment, the power source 48 is a battery that is provided locally with the sensing device 30. The battery may have any suitable construction/composition, including, but not limited to a nickel metal hydride (NiMH) composition or a lithium-ion (Li-ion) composition. Physically, the battery may be provided as a portion of an integrated package together with the processor 42 and/or wireless communication circuitry 44, though this packaging configuration is not strictly necessary. In some embodiments, to provide a complete, singular device, the battery and/or any integrated packaging may be directly affixed to the carrier material 32. In doing so, the power source is local to and coupled with the sensing device 30, thus reducing the need for a wired connection to the device 30.

The wireless communication circuitry 44 may include any combination of signal processors, power amplifiers, signal filters, transceivers, and the like that may be required to digitally communicate with a physically separate device via the coupled antenna 46. In some embodiments, the antenna 46 may include one or more conductive fibers or films that are integrated with/on the carrier material 32. In other embodiments, the antenna 46 may be internal to the communication circuitry 44. As further illustrated in FIG. 2, in some embodiments, the antenna 46 may be located at a distal end portion of the sensing device 30, which may surround or abut a distal end portion of the subject's limb. Locating the antenna 46 in this manner may position it apart from large, fluidly-dense bodies, such as the subject's torso, which could attenuate and/or distort transmission signals.

The communication between the antenna 46 and the communication circuitry 26 of the host system 20 may be unidirectional or bi-directional, and may be performed according to one or more established or subsequently developed radio frequency (RF) protocols. Suitable RF protocols may include those according to IEEE 802.11, IEEE 802.15, a Bluetooth standard, a ZigBee standard, near-field communication (NFC) standards, RFiD or the like.

The wireless communication circuitry 44 may generally operate at the direction of the processor 42 and/or on the basis of digital information supplied by the processor 42. In some embodiments, the wireless communication circuitry 44 may be the sole manner of digitally communicating to/from the sensing device 30. For the purpose of this disclosure, it should be noted that "digitally communicating" is not intended to encompass visual or audible alerts that may be communicated directly from the device 30 to the surgical team.

Figure 3:
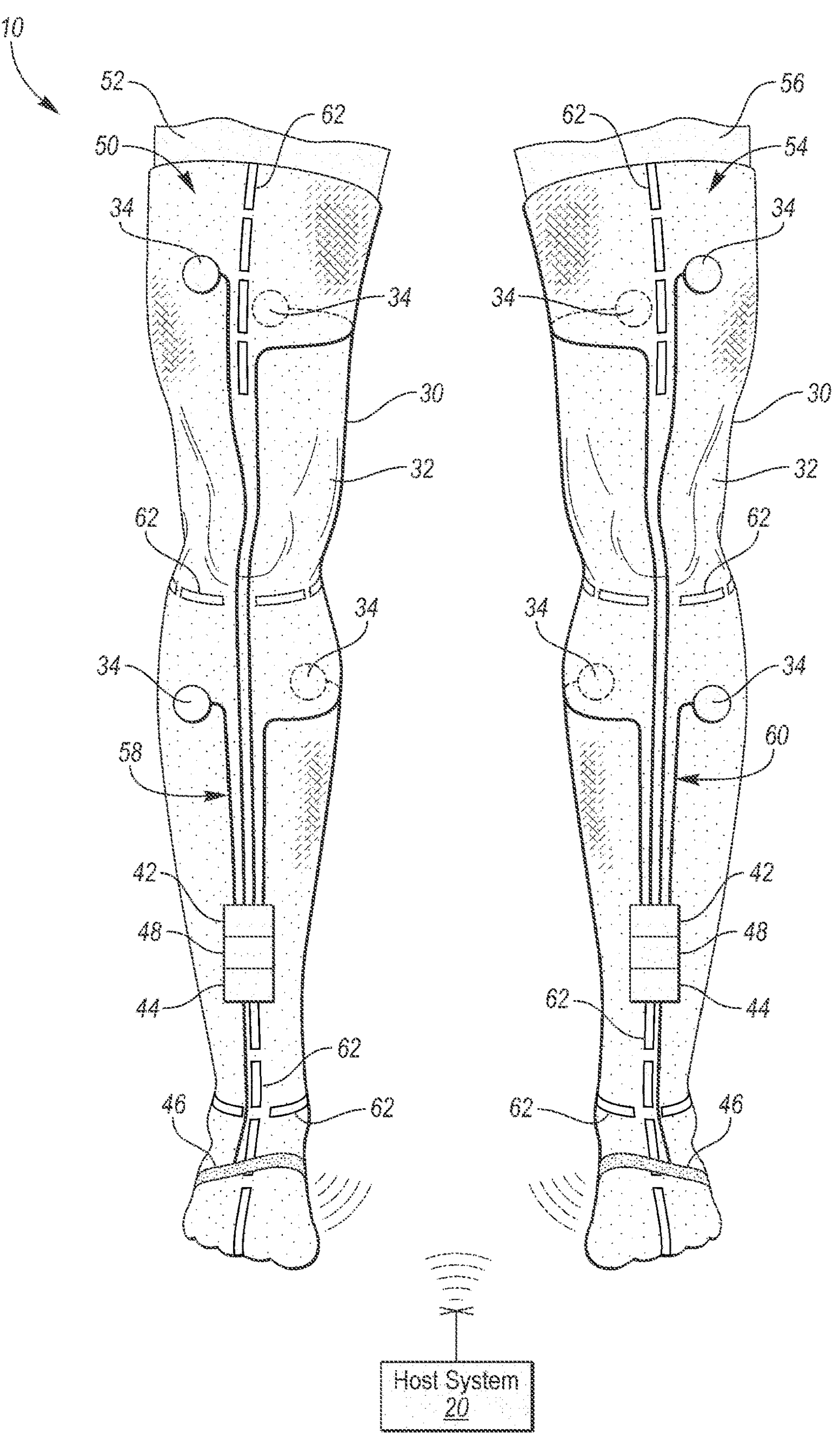
FIG. 3 is a schematic anterior view of a first sensing device provided on a first leg of a subject a second sensing device provided on a second leg of the subject, and host system in communication with the first sensing device and the second sensing device.

As shown in FIG. 3, when multiple sensor devices 30 are utilized concurrently, each sensor device 30 may maintain its own local sensor-level network while also wirelessly communicating to the host system 20 via device-specific wireless communications circuitry 44. An example of such a scenario might be if the system 10 was required to monitor both of the subject's legs for neuromuscular activity. At a network level, in order for each device to transmit event data to the host system 20 concurrently, the system 10 may utilize a wireless communications protocol that has the capability of managing data flow from a plurality of different sources on the network, as opposed to one that relies on 1-to-1 pairing relationships.

In the embodiment provided in FIG. 3, a first sensor device 50 is provided on a first limb 52, and a second sensor device 54 provided on a second limb 56. Each device 50, 54 may include separate wireless communication circuitry 44 that may be in wireless digital communication with an adjacent host station 20. If required, typical network infrastructure (e.g., a switch or router) may be provided to modulate communications between the various devices. As shown, the first sensor device 50 may manage a first array 58 of neuromuscular sensors 34, and the second sensor device 54 may monitor a second array 60 of neuromuscular sensors 34. As noted above, in a preferred embodiment, some or all of the neuromuscular sensors 34 may include sensors capable of sensing a mechanical motion and then generating an electrical output signal representative of that sensed motion (i.e., a mechanomyography signal).

In embodiments utilizing a carrier material 32 to position the sensor array with respect to the subject, the specific nature of the carrier material 32 may vary based on the location of the surgical site and nature of the surgical procedure. In many cases the carrier material 32 may resemble a cuff or sleeve that is secured around a limb of the subject. Such a design may be suitable, for example, with a spinal procedure where nerves existing within the surgical site are known to innervate peripheral muscles of the arms or legs.

To assist the medical staff in achieving proper alignment of the sleeve on the leg of the subject, the carrier material 32 may include one or more alignment indicia 62 from which relative orientation may be quickly identified. These indicia 62 may include, anatomical markers, such as indications or holes for a knee cap or ankle bone, marks to align with other equipment, marks to align with anatomical reference planes or the like. In one embodiment, the indicia 62 may include a line that extends along a majority of the length of the stocking/sleeve, and/or at certain anatomical waypoints along the length of the limb, such as shown in FIG. 3. In this embodiment, the line(s) may provide a quick visual reference to determine overall relative orientation of the sleeve, while also calling attention to any localized twisting.

In some embodiments, the carrier material 32 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 32 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 32 may include, for example, a blood pressure cuff worn around the subject's arm (or else may include functionality similar to that of a standard blood pressure cuff). In these examples, the carrier material 32 serves a function outside of that of a dedicated neuromuscular sensing device, and thus provides efficiencies in pre-op preparation and planning, while also allowing monitoring access on sometimes crowded limbs.

As noted above, the system 10 may further include one or more elongate medical instruments 70 (i.e., stimulators 70) that are capable of selectively providing a stimulus 72 within the intracorporeal treatment area 12 of the subject 14. For example, in one configuration, the elongate medical instrument 70 may include a probe 76 (e.g., a ball-tip probe, k-wire, or needle) that has an electrode 78 disposed on a distal end portion. The electrode 78 may be selectively electrified, at either the request of a user/physician, or at the command of the processor 28, to provide an electrical stimulus 72 to intracorporeal tissue of the subject. In other configurations, the elongate medical instrument 70 may include a dilator, retractor, clip, cautery probe, pedicle screw, or any other medical instrument that may be used in an invasive medical procedure. Regardless of the instrument, if the intended artificial stimulus is an electrical current, the instrument 70 may include a selectively electrifiable electrode 78 disposed at a portion of the instrument that is intended to contact tissue within the intracorporeal treatment area 12 during the procedure.

During a surgical procedure, the user/surgeon may selectively administer the stimulus to intracorporeal tissue within the treatment area 12 to identify the presence of one or more nerve bundles or fibers. For an electrical stimulus 72, the user/surgeon may administer the stimulus, for example, upon depressing a button or foot pedal 74 that is in communication with the host system 20. The electrical stimulus 72 may, for example, be a periodic stimulus that includes a plurality of sequential discrete pulses (e.g., a step pulse) provided at a frequency of less than about 10 Hz, or from about 1 Hz to about 5 Hz, and preferably between about 2 Hz and about 4 Hz. Each pulse may have a pulse width within the range of about 50 μs to about 400 μs. In other examples, the discrete pulse may have a pulse width within the range of about 50 μs to about 200 μs, or within the range of about 75 μs to about 125 μs. Additionally, in some embodiments, the current amplitude of each pulse may be independently controllable.

If a nerve extends within a predetermined distance of the electrode 78, the electrical stimulus 72 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, the impedance between the electrical stimulus and the ground patch, and the magnitude of the stimulus current. In one configuration, a lookup table or other suitable function may be employed to provide an approximate distance between the electrode and the nerve, given a known stimulus magnitude and a measured mechanical muscle response.

Once the sensing devices are properly positioned on the subject 14, the system 10 may generally operate by applying a stimulus 72 to an intracorporeal treatment area 12 of the subject 14 via the stimulator 70, and then monitoring the resulting neuromuscular activity to determine the existence of an artificially induced muscle response and quantify the same. In some embodiments, based on input from the sensing device 30, the host system 20 may be configured to alert a surgeon to a detected induced muscle response, to indicate a determined distance between the stimulator and a nerve, to display one or more signal traces representative of the sensed muscle response(s), to record event information for subsequent review and analysis, and/or to perform other ancillary functionality.

While it is important to transmit data to the host system 20 for display, analysis, and/or recordation purposes, the unconstrained transmission of continuous and full resolution sensor data, however, can result in a significant power draw that may quickly deplete onboard power supply 48. As such, in some embodiments, the on-board device processor 42 may be operative to pre-process, filter, and/or down-sample the raw sensor output in a manner that minimizes the amount of information that is required to be streamed from the sensor device 30 to the host system 20. In one embodiment, this on-board processing may involve pre-detecting events, and transmitting only sensor data that likely represents an induced neuromuscular response. In another embodiment, this on-board processing may involve transmitting sensor data representative of an induced neuromuscular response at a first resolution and/or sampling rate and transmitting all other sensor data at a second, comparatively slower or lower resolution and/or sampling rate.

Figure 4:
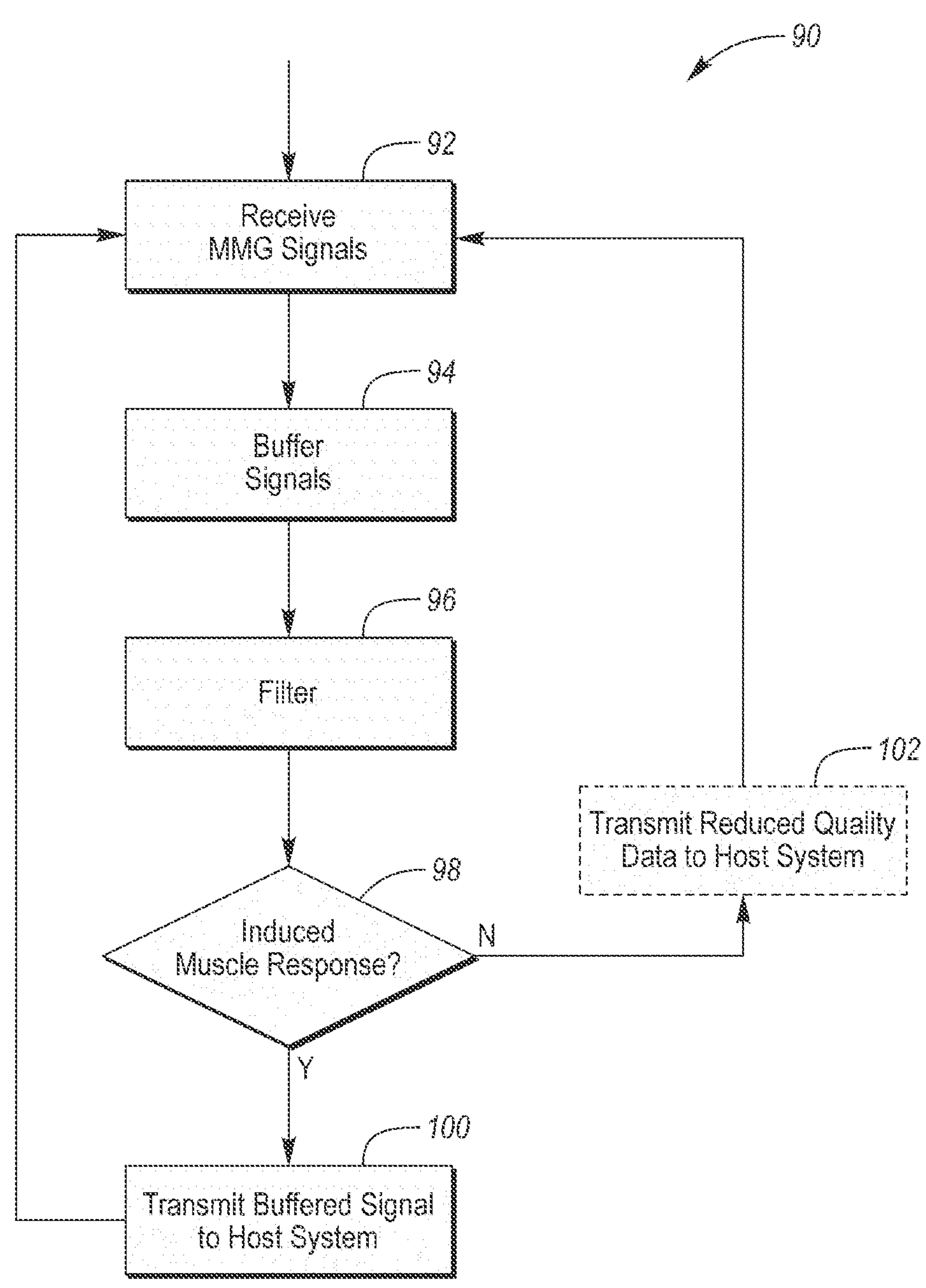
FIG. 4 is a schematic flow diagram for locally processing a plurality of MMG output signals to reduce total data transmission throughput.

FIG. 4 schematically illustrates a method 90 of locally processing a plurality of MMG output signals 38 to reduce total data transmission throughput from the wireless communication circuitry 44. The method 90 is performed by the device processor 42 and begins by the processor 42 receiving each MMG output signal generated by the plurality of neuromuscular sensors 34 (at 92) and storing a portion of each signal (i.e., buffering) into electrically erasable memory associated with the processor 42 (at 94) for further analysis. The portion of each signal that is recorded at 94 may either be a rolling period of time that follows a first-in-first-out scheme as new data is received, or else may be a triggered period of time that begins at or shortly after the occurrence of some event (e.g., a stimulation). In another embodiment, a rolling period of time may continuously be buffered upon receipt, then filtered to remove portions of the signal that have a high probability of not representing an induced muscle response, and a triggered period of time may then be buffered from this filtered rolling window for further analysis.

In one embodiment, the triggered period of time may begin at or very shortly after the administering of a stimulus 72 by the stimulator 70. Such a strategy is premised on the idea that induced muscle responses occur following the administration of a stimulus, and if no stimulus has been provided, it is unlikely that any sensed motion represents an induced response. Similarly, if a stimulus has been provided and no muscle response is detected within an expected window of time following the stimulus, it is likely that the stimulus was either too weak or too distant from a nerve to cause that nerve to depolarize.

The length/duration of the buffered portion of each signal may either be fixed or variable according to one or more attributes of the subject 14 and/or of the signal itself. Relevant attributes of the patient that could affect the duration of the response window include the subject's body mass index (BMI), or the existence of diabetes, neuropathy, degenerative nerve conditions, muscle fatigue, or other such factors that are known to affect nerve conduction velocity and/or muscular response. Likewise, one relevant attribute of the signal that could be used to alter the duration of the window includes, for example, the initial slope of the acceleration profile when movement is first detected. In an effort to limit the amount of information that must be subsequently processed, the length of the buffered data should be from about 75 ms to about 300 ms, or even more narrowly from about 100 ms to about 200 ms.

Prior to any analysis, it may be beneficial to filter the MMG output signals (at 96) to eliminate signal content that is not likely representative of an artificially induced muscle response. This filtering may include, for example, the application of a high pass filter, low pass filter, removal of signal content that is persistent across and seemingly uninfluenced by the application of multiple stimuli, or signal content that is otherwise attributable to a gross translation or rotation of the limb.

In one embodiment, the processor 42 may detect gross translations or rotations by virtue of having a plurality of mechanical sensors 36 held in varying positions around the limb by the carrier material 32. More specifically, if each of the plurality of sensors 36 output a respective signal 38 that, when viewed collectively suggests a coordinated translation or rotation (i.e., a global motion rather than a local motion), any signal content specific to that global motion can be digitally removed. To accomplish this motion detection, the local processor 42 may begin by ensuring that the received signals are coordinated in time (e.g., through the use of time-stamps upon receipt, clock synchronization, or other buffering or signal processing techniques). The processor 42 may then examine the collection of MMG output signals to identify any motion that is common between the sensors or that is otherwise indicative of a gross translation or rotation of the limb. If any such motion is identified, it may be filtered, attenuated, or otherwise removed from each respective output signal 38 prior to the system performing any further analysis.

In some embodiments, the processor 42 may perform this gross motion rejection by mapping each sensor reading to a three dimensional (virtual) solid model of the limb. This mapping may be accomplished by understanding the number and relative placement of the sensors on the device 30, and by mapping the actual sensed motion to corresponding points on a virtual solid model of the limb. In some embodiments, the processor 42 may receive an indication of the subject's anatomy (e.g., body mass index (BMI), limb circumference, or percent body fat) to scale the size and presumed elastic modulus of the virtual solid model. The global motion may then be extracted from the model, for example, by examining the motion of, for example, the centroid of the model or of a rigid body diagram/representation of the limb.

In some embodiments, using a virtual limb model may not only enable gross motion detection by inspecting the motion of the model, itself, but it may also permit virtual sensor points to be dropped on the model, which may provide a more complete/higher resolution picture of how the limb is responding/moving. This better understanding of the limb motion may then enable greater accuracy when detecting the occurrence and magnitude of an artificially neuromuscular response, while also serving to reduce the overall noise floor of the system.

With continued reference to FIG. 4, following any filtering (at 96) the processor 42 may determine (at 98) if the MMG output signal 38 from any one or more of the plurality of sensors 34 is representative of an artificially induced neuromuscular response. If the processor 42 concludes that the output signal 38 is representative of an induced response, processor 42 may transmit one or more of the buffered MMG output signals 38 to the host system 20 via the wireless communication circuitry 44 (at 100). If this determination is not decided in the affirmative, in one embodiment, the processor 42 may continue buffering and analyzing in a continuous manner while not transmitting anything to the host system 20 (i.e., the processor 42 would transmit the one or more buffered MMG outputs signals only if the MMG output signal from one or more of the plurality of mechanical sensors is determined to be representative of an artificially induced neuromuscular response). As mentioned above, in another embodiment (designated by the lines in phantom), the processor 42 may continue to transmit signal data (at 102) to the host system 20 even if no event is detected. In such an embodiment, the processor 42 may reduce the sampling frequency and/or digital resolution of any signal data that is not believed to be representative of an induced muscle response prior to transmitting. Conversely, if an induced response is detected, the processor 42 may transmit comparatively higher quality data (i.e., faster sampling rate and/or greater resolution) to the host system 20 for display, further analysis, and/or recordation.

To determine whether the MMG output signal is representative of an artificially induced neuromuscular response (at 98), in some embodiments, the processor 42 may be configured to automatically perform one or more signal processing algorithms or methods to determine whether a mechanical movement sensed embodied by an output signal 38 is representative of an artificially-induced mechanical muscle response or if it is merely a subject-intended muscle movement and/or an environmentally caused movement. These processing algorithms may be embodied as software or firmware, and may either be stored locally on the processor 42, or may be readily assessable by the processor 42.

In some embodiments, the signal processing algorithms used to recognize an induced response may involve one or more analog detection techniques such as described, for example, in U.S. Pat. No. 8,343,065, issued on Jan. 1, 2013 (the '065 Patent), which is incorporated by reference in its entirety, one or more digital detection techniques, such as described in US 2015/0051506, filed on Aug. 13, 2013 (the '506 Application), which is incorporated by reference in its entirety, and/or one or more triggered techniques, which are described above and in U.S. patent application Ser. No. 15/995,879, filed on Jun. 1, 2018, which is incorporated by reference in its entirety. In the analog techniques, the processor may examine one or more aspects of the MMG output signal 38 in an analog/time domain to determine if the sensed response is an artificially-induced response of the muscle to the stimulus. These analog aspects may include, for example, the time derivative of acceleration, or the maximum amplitude of the initial response. In one specific embodiment, the processor 42 may indicate that the sensed motion is likely representative of an induced muscle response if the time derivative acceleration of the output signal (i.e., the initial rise slope of the primary muscle contraction) exceeds a predefined threshold.

In a digital context, such as described in the '503 Application, the processor may compare the frequency components of the MMG output signal (i.e., using the signal converted into the frequency domain) with the frequency of the applied stimulation to determine whether the sensed motion and/or candidate events were induced by the applied stimulus. Such a technique may be made more robust by considering only events or muscle activity that occurs within the period of time following the stimulus where an induced response is likely to occur and/or by aggressively filtering/attenuating or ignoring the signal outside of expected periods of time prior to applying the signal processing algorithms.

In some embodiments, the signal processing algorithms may include one or more supervised learning algorithms that are operative to classify any sensed motion into one of a plurality of classifications that include at least whether the motion is, or is not representative of an artificially-induced mechanical response of the muscle. Both classifications may provide valuable information to an operating surgeon during a procedure. Affirmatively detecting a response informs the surgeon that a nerve is proximate to the stimulator/tool, and to proceed with caution. Conversely, determining that no induced response occurred, particularly if a stimulus is provided, informs the surgeon that the nerve is not present and they can proceed in their normal manner.

In a general sense, a supervised learning algorithm is an algorithm that attempts to classify a current sample using observations made about prior samples and their known classifications. More specifically, the algorithm attempts to construct and/or optimize a model that is capable of recognizing relationships or patterns between the training inputs and training outputs, and then the algorithm uses that model to predict an output classification given a new sample. Examples of supervised learning algorithms that may be employed include neural networks, support vector machines, logistic regressions, naive Bayes classifiers, decision trees, random forests, or other such techniques or ensembles of techniques.

Figure 5:
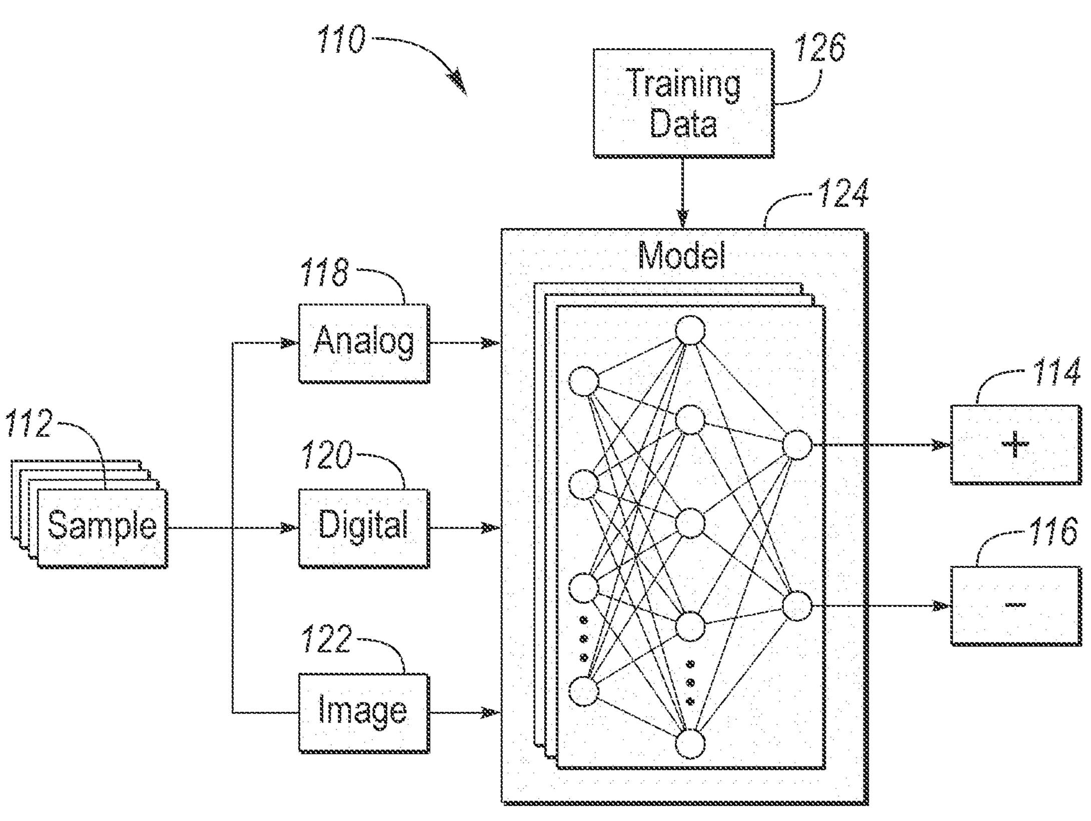
FIG. 5 is a schematic diagram of a signal processing algorithm, including a supervised learning algorithm, for classifying a sensed muscle motion as being either an induced response or not an induced response.

FIG. 5 schematically illustrates an embodiment of a supervised learning algorithm 110 that may be used to classify one or more buffered periods of the MMG output signal(s) 38 into a binary classification (i.e., an artificially induced muscle response 112, or not an artificially induced response 114). While the supervised learning algorithm 110 may certainly be applied on a sensor-by-sensor basis (which may aid in classifying the output from any one sensor channel), in one embodiment, the algorithm 110 may consider the MMG output signals 38 from a plurality of the sensors 34, collectively (e.g., within the analysis buffer as described above). Such a strategy may recognize that a muscle response on a first side of the limb may cause a detectable response in one or more sensors located apart from that muscle by virtue of wave propagation and/or via the dynamics of the limb itself. Furthermore, nerve roots and nerve bundles often serve to innervate multiple muscle groups, though each to varying degrees. Thus, one manner of detecting the induced depolarization of a nerve is to examine the coordinated responses of all muscles the stimulated nerve innervates. Such a multi-channel analysis is generally well suited for supervised learning algorithms.

With continued reference to FIG. 5, the processor 42 may initially characterize the one or more MMG output signals 38/buffered samples and/or any recognized muscle motion according to one or more analog characteristics 118, frequency characteristics 120, and/or time-series/image characteristics 122. The processor may then use a model 124 constructed and/or optimized on the basis of a plurality of pre-classified training samples 126 to make an informed classification that minimizes an established error function or maximizes the probability of an accurate prediction.

In an embodiment, the one or more analog characteristics 118 may include, for example, max/min acceleration amplitudes, max/min velocity amplitudes, time derivative of acceleration, signal rise time, or curve fitting coefficients. Likewise, the one or more frequency characteristics 120 may include, for example, FFT coefficients, peak frequencies, peak frequency magnitudes, harmonic frequencies, or frequency fall-off. Finally, the time-series/image characteristics 122 may include a snapshot of a graph of the MMG output 38 over time. In general, as discussed in the '065 Patent and in the '506 Application, artificially-induced muscle responses have certain analog and frequency characteristics that non-induced responses do not. As such, the supervised learning algorithm 110 may model these characteristics 118, 120 in the aggregate to predict the nature of the muscle event with a greater accuracy. Furthermore, in some situations, the visual attributes of an induced response may tell a more complete story than any one parameter or collection of parameters could. As such, in an embodiment, the supervised learning algorithm 110 may include an image based classifier that may attempt to classify a muscle response on the basis of a visual similarity with other previously identified induced responses.

In some embodiments, the supervised learning algorithm 110 may employ an ensemble approach to generating the output classification. In such an approach, the model 124 may include a plurality of different models/approaches that may be combined according to a weighting/costing formula to provide improved redundancy/voting. In another embodiment, the ensemble approach may use the output of one or more approaches/models as an input of another model. For example, the analog and/or frequency based detection techniques discussed in the '065 Patent and/or in the '506 Application may output a probability or likelihood that an event in question is representative of an induced response. These estimations may then be fed into, for example, a supervised learning algorithm as another input (i.e., where the supervised learning algorithm may understand situations when the pre-determined algorithms are to be trusted or not trusted). In another embodiment, each model, including any supervised learning algorithm may feed into a separate algorithm that may output a binary response or probability based upon the outcomes of the various models. This approach may use voting algorithms, probability combinations, and/or separate supervised learning algorithms to provide an output based on the prediction of each constituent model.

In one configuration, the processor 42 may examine each received output signal 38 individually to see if any respective output signal exhibits traits that are likely the product of an induced muscle response. The processor 42 may also collectively examine all received output signals 38 to determine if the motion/response of various portions of the limb, together, suggest the occurrence of an induced muscle response. In one configuration, the processor 42 may initially screen each output signal individually to determine if any one or more output signals are indicative of the occurrence of an artificially induced neuromuscular response. This initial screening may occur by examining the output signals in real-time or following the application of one or more filtering/noise reduction techniques. If any one or more of the output signals appear to represent and induced muscle response, the process of 42 may then collectively analyze a plurality of the buffered output signals to determine if the coordinated response is also indicative of an induced muscle response. If the signals individually and collectively indicate an induced muscle response, the processor 42 may then transmit the buffered signals to the host system 20 (at 100 in FIG. 4).

In some embodiments, the sensing device 30 may include a resident alert system that is operative to provide one or more visual and/or audible alerts to a surgeon or surgical team. The alert system may be embodied as a combination of software/firmware executed by the processor 42 in combination with hardware configured to illuminate and/or broadcast an audible signal. For example, FIG. 2 illustrates a plurality of lighting elements 130, such as light emitting diodes, that may illuminate at the direction of the processor 42 or other monitoring circuitry associated with the sensor 34 itself.

In one configuration, the alert system may be configured to provide a first alert 132 if one or more of the MMG output signals 38 is indicative of the occurrence of an artificially induced neuromuscular response, and provide a second alert 134 if the plurality of the buffered MMG output signals are collectively indicative of the occurrence of an artificially induced neuromuscular response. The first alert 132 may be, for example, be a light that is illuminated on the particular sensor 34 that sensed the induced response. Likewise, the second alert 134 may be, for example, illuminating a plurality of lights across all of the sensors 34 (i.e., to indicate collective detection).

In one configuration the first alert 132 may be different in at least one of tone or color from the second alert 134 to draw attention to the differences. Likewise, in one configuration, the alert system may include a both a light source provided with each sensor and a speaker provided with the device 30. The first alert 132 may include a first color illuminated from a first light source provided with the sensor 34 that generated the MMG output signal indicative of the artificially induced neuromuscular response and may further include a first alert tone played via the speaker. The second alert 134 may then include at least one of: a second color illuminated from the first light source and a second alert tone played via the speaker; or a third color illuminated from a second light source provided apart from the sensor 34 that generated the MMG output signal indicative of the artificially induced neuromuscular response and a second alert tone played via the speaker. In some embodiments, the first color is different from the second color, the first tone is different from the second tone, and the third color is the same or different from the first color.

In the embodiment where data transmission is paused if an induced response is not detected (i.e., as opposed to simply being down-sampled), unless guarded against, it may be possible for a drop in wireless signal quality or transmission to be construed as representing a lack of an induced response, even if an induced response is occurring and has been actively detected by the device 30. In such a scenario, a surgeon may continue with a procedure while being unaware that a nerve is in close proximity to his/her surgical instrument. This lack of awareness maybe partially remedied by including the above-described alert system on the sensing device 30 itself. In such an embodiment, the communication of an alert via the device 30 would not be contingent on the existence or quality of the wireless connection between the device 30 host system 20, and the surgeon's attention may be called to the discrepancy between what the device is alerting to and what the host system 20 might be displaying.

In some embodiments, the quality and/or existence of the wireless connection may be evaluated by periodically transmitting a connection diagnostic data packet between the device 30 and the host system 20. This data packet maybe a low-footprint, nominal transmission that is performed solely to evaluate whether the connection is still active and/or whether the fidelity of the connection is sufficient to convey data promptly to the host system 20. In some embodiments, the diagnostic data packet may be a checksum that may validate the previously transmitted data, a time stamp, or similar de minimis transmissions.

In one embodiment the sensing device 30 may transmit the connection diagnostic packet on a regular, periodic interval. The host system 20 may utilize the existence and/or content of the received connection diagnostic packet to evaluate the connection, and alert a surgeon that it may not be proper to infer that a lack of a response/alert is the result of a lack of an induced muscle response. Instead, the lack of a response might the result of a compromised wireless connection between the host system and the sensing device. If the host system 20 detects that the wireless connection has been broken or if it is of such a low quality that alerts to the surgical team may be compromised, the host system 20 may proactively provide a visual and/or audible alert to the surgical team so that the connection maybe repaired or other precautions taken. In another embodiment, the host system 20 may be operative to transmit the connection diagnostic packet to the sensing device 30 on a regular, periodic interval. In such an embodiment, if the wireless communication circuitry 44 and/or processor 42 do not receive this packet when expected, the processor 42 may provide a visual and/or audible alert via the alert system described above.

Figure 6:
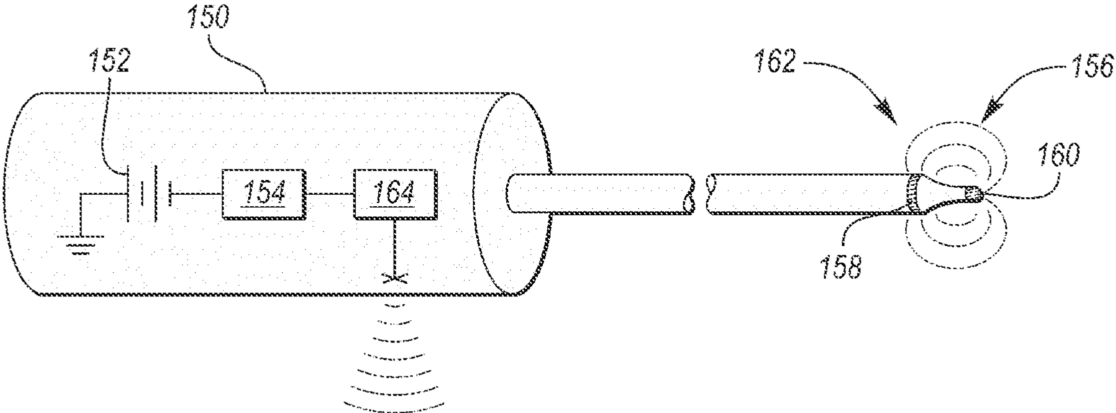
FIG. 6 is a schematic side view of a wireless bi-polar stimulator probe.

As schematically shown in FIG. 6, in one embodiment, in addition to a wireless sensing device 30, the system 10 may include a wireless stimulator 150. In one configuration, the wireless stimulator 150 may include a power supply 152 and control circuitry 154 that is operative to administer an electrical stimulus 156 in a bi-polar manner between two electrodes 158, 160 provided on a distal end portion 162 of the stimulator 150.

In one configuration, the wireless stimulator 150 may include communication circuitry 164 that enables it to wirelessly communicate with the host system 20 and/or the sensor device 30. In such an embodiment, the magnitude and/or the frequency of the stimulus 156 maybe adjusted according to one or more control signals received via the communication circuitry 164. Additionally, in some embodiments, the communication circuitry 164 may transmit an indication that a stimulus has been applied via of the electrodes 158, 160. This provided indication may be received, for example, by the host system 20 and/or communicated to the sensing device 30 to enable the sensing device 30 to begin buffering the received MMG output signals 38 for further analysis.

In an embodiment where the host system 20 and/or stimulator 70, 150 does not provide the sensing device 30 with an indication that a stimulus has been administered, the sensing device 30 may still be capable of recognizing the occurrence of the stimulus by monitoring changes in one or more electrical parameters of the subject. More specifically, when an electrical stimulus is applied to the body, the electrical potential of all tissue within the body may momentarily change. When monitored in an electromyography context, such an inrush is generally referred to as a stimulus artifact. While a stimulus artifact is generally viewed as a negative quality (i.e., it can complicate electromyography measurements and potentially obscure changes in the muscle action potential), when used with MMG, the stimulus artifact may provide a near real-time indication that a stimulus has been administered.

Figure 7:
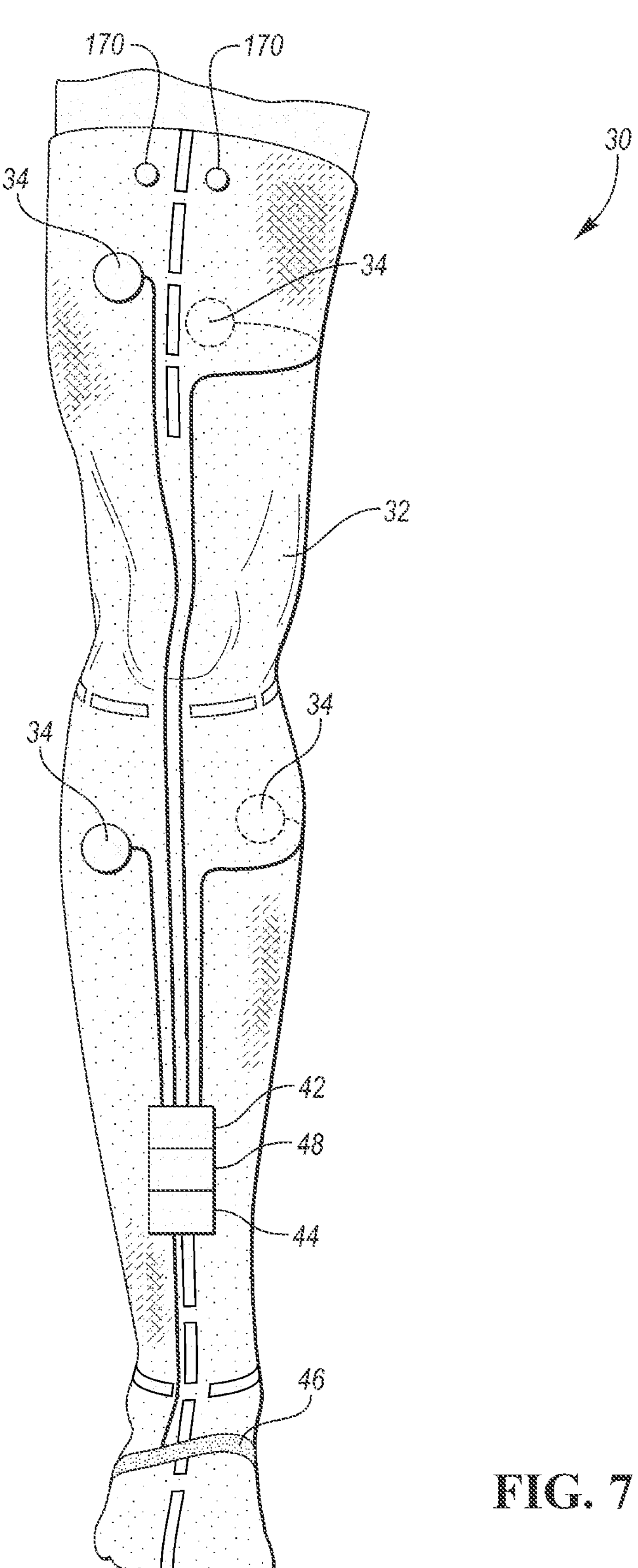
FIG. 7 is a schematic anterior view of a sensing device provided on a leg of a subject with a pair of electrodes for monitoring an electrical parameter of the leg.

Therefore, in one embodiment, such as shown in FIG. 7, the sensing device 30 may include a pair of electrodes 170 in communication with the processor 42 for the purpose of monitoring one or more electrical parameters of the subject 14. Using these electrodes 170, the processor 42 may be configured to identify the occurrence of a an electrical stimulus 72, 156 provided apart from the device 30 by recognizing a momentary change in one or more of the monitored parameters (i.e., evidence of a stimulus artifact). These electrodes 170 may include any combination of skin-applied transdermal electrodes and invasive needle electrodes. For example, in one embodiment the pair of electrodes 170 may include two spaced transdermal electrodes held in contact with the skin of the subject 14. In another embodiment the pair of electrodes 170 may include one needle electrode extending through the skin, and one transdermal electrode. Finally, in one embodiment, the pair of electrodes 170 may include two spaced needle electrodes. As noted above, in one configuration, the processor 42 may begin buffering the plurality of MMG output signal 38 following the identification of the electrical disturbance and/or stimulus artifact.

While the best modes for carrying out the present technology have been described in detail, those familiar with the art to which this technology relates will recognize various alternative designs and embodiments that are within the scope of the appended claims. It is intended that all matter contained in the above description or shown in the accompanying drawings shall be interpreted as illustrative only and not as limiting.

Various advantages and features of the disclosure are further set forth in the following clauses:

Clause 1: A sensing device for detecting an artificially induced neuromuscular response within a limb of a subject, the sensing device comprising: a plurality of mechanical sensors, each operative to monitor a mechanical response of a different muscle group of the limb and to generate a mechanomyography (MMG) output signal corresponding to the monitored motion; wireless communication circuitry operative to transmit digital information to a host system via radio frequency (RF) communication; and a processor in electrical communication with each of the plurality of mechanical sensors, and with the wireless communication circuitry, wherein the processor is configured to: receive and buffer a portion of each MMG output signal; determine if the MMG output signal from any one or more of the plurality of mechanical sensors is representative of an artificially induced neuromuscular response; and transmit one or more of the buffered MMG output signals to the host system via the wireless communication circuitry only if the MMG output signal from one or more of the plurality of mechanical sensors is determined to be representative of an artificially induced neuromuscular response.

Clause 2: The sensing device of clause 1, wherein the buffered MMG output signals have a first resolution and a first sampling rate; and the processor further configured to generate a low-quality representation of each of the buffered MMG output signals, the low-quality representation having a second resolution and a second sampling rate such that at least one of: the second resolution is less than the first resolution; or the second sampling rate is less than the first sampling rate; and wherein the processor is configured to transmit each of the low-quality representations to the host system via the wireless communication circuitry if the MMG output signals are not representative of an artificially induced neuromuscular response.

Clause 3: The sensing device of any of clauses 1-2, wherein the digital information includes a connection diagnostic packet that is transmitted on a regular, periodic interval; and wherein the host system may utilize the connection diagnostic packet to determine if a lack of a transmitted buffered MMG output signal is indicative of a lack of an artificially induced neuromuscular response or if it is indicative of a compromised wireless connection between the host system and the sensing device.

Clause 4: The sensing device of any of clauses 1-3, wherein the wireless communication circuitry is operative to receive a connection diagnostic packet on a regular, periodic interval from the host system; and wherein the processor is configured to provide an alert if the connection diagnostic packet is not received at the periodic interval.

Clause 5: The sensing device of any of clauses 1-4, wherein the processor is operative to: receive an indication that a stimulus has been provided to the subject; and buffer a portion of each MMG output signal only following the receipt of the indication.

Clause 6: The sensing device of any of clauses 1-5, further comprising a pair of electrodes operative to be placed in electrical communication with the limb and to monitor an electrical parameter of the limb; and wherein the processor is operative to: detect a change in the electrical parameter of the limb, the change in the electrical parameter being indicative of an electrical stimulus applied to the subject; and buffer a portion of each MMG output signal only following the detection of the change in the electrical parameter.

Clause 7: The sensing device of any of clauses 1-6, wherein the processor is configured to determine if the MMG output signal from any one or more of the plurality of mechanical sensors is representative of an artificially induced neuromuscular response by: analyzing each MMG output signal individually to determine if one or more of the MMG output signals is indicative of the occurrence of an artificially induced neuromuscular response; and analyzing a plurality of the buffered MMG output signals collectively to determine if the plurality of the buffered MMG output signals are indicative of the occurrence of an artificially induced neuromuscular response.

Clause 8: The sensing device of clause 7, wherein the plurality of the buffered MMG output signals are only analyzed by the processor if it is determined that one or more of the MMG output signals is indicative of the occurrence of an artificially induced neuromuscular response.

Clause 9: The sensing device of any of clauses 7-8, wherein analyzing each MMG output signal individually includes at least one of: comparing an analog, time-domain parameter of the MMG output signal to a threshold; determining a fundamental frequency or harmonic of the MMG output signal; or examining one or more characteristics of the MMG output signal using a supervised learning algorithm.

Clause 10: The sensing device of any of clauses 7-9, wherein the processor is configured to determine that the MMG output signal from any one or more of the plurality of mechanical sensors is representative of an artificially induced neuromuscular response if it is determined that both: one or more MMG output signal individually indicates the occurrence of an artificially induced neuromuscular response; and the plurality of the buffered MMG output signals collectively indicate the occurrence of an artificially induced neuromuscular response.

Clause 11: The sensing device of any of clauses 7-10, wherein the processor is further configured to filter each of the MMG output signals to attenuate a portion of the MMG output signal that is attributable to gross translation or gross rotation of the limb; and wherein the filtering occurs prior to analyzing each MMG output signal individually.

Clause 12: The sensing device of any of clauses 7-11, further comprising an alert system configured to: provide a first alert if one or more of the MMG output signals is indicative of the occurrence of an artificially induced neuromuscular response; and provide a second alert if the plurality of the buffered MMG output signals are indicative of the occurrence of an artificially induced neuromuscular response.

Clause 13: The sensing device of clause 12, wherein the first alert is different in at least one of tone or color from the second alert.

Clause 14: The sensing device of any of clauses 12-13, wherein the alert system includes a light source provided with each mechanical sensor and a speaker; wherein the first alert includes a first color illuminated from a first light source provided with the mechanical sensor that generated the MMG output signal indicative of the artificially induced neuromuscular response and a first alert tone played via the speaker; and wherein the second alert includes at least one of: a second color illuminated from the first light source and a second alert tone played via the speaker; or a third color illuminated from a second light source provided apart from the mechanical sensor that generated the MMG output signal indicative of the artificially induced neuromuscular response and a second alert tone played via the speaker; wherein the first color is different from the second color, the first tone is different from the second tone, and the third color is the same or different from the first color.

Clause 15: The sensing device of any of clauses 1-14, further comprising a carrier material operative to be secured around a portion of the limb of the subject, wherein each of the plurality of mechanical sensors are secured to the carrier material.

Clause 16: The sensing device of clause 15, wherein the carrier material is a sleeve; and wherein the wireless communication circuitry includes an RF antenna provided on a distal end portion of the sleeve.

Clause 17: The sensing device of any of clauses 1-16, wherein the RF communication includes communication according to at least one of an IEEE 802.11, an IEEE 802.15, or a Bluetooth protocol.

Clause 18: A system for detecting the presence of a nerve within an intracorporeal treatment area of a subject, the system comprising: a host system including a display; a first sensing device including: a first plurality of mechanical sensors, each operative to monitor a mechanical response of a different muscle group of a first portion of the subject and each configured to generate a respective mechanomyography (MMG) output signal corresponding to the monitored motion; and a first processor in communication with each mechanical sensor of the first plurality of mechanical sensors and configured to receive each of the generated MMG output signals from the first plurality of mechanical sensors; and a second sensing device including: a second plurality of mechanical sensors, each operative to monitor a mechanical response of a different muscle group of a second portion of the subject and each configured to generate a respective mechanomyography (MMG) output signal corresponding to the monitored motion; and a second processor in communication with each mechanical sensor of the second plurality of mechanical sensors and configured to receive each of the generated MMG output signals from the first plurality of mechanical sensors; and wherein each of the first processor and second processor are in wireless digital communication with the host system and are each operative to wirelessly transmit at least a portion of one or more MMG output signals to the host system for output via the display.

Clause 19: The system of clause 18, wherein each of the first processor and second processor are operative to transmit a respective connection diagnostic data packet to the host system on a repeating periodic interval; and wherein the host system is configured to provide an alert if the connection diagnostic data packet is not received from one or both of the first processor or second processor on the repeating periodic interval.

Clause 20: The system of any of clauses 18-19, wherein the first processor is operative to determine if the MMG output signal from any one or more of the first plurality of mechanical sensors is representative of an artificially induced neuromuscular response, and to transmit a portion of the one or more MMG output signals only if it is determined that the MMG output signal from any one or more of the first plurality of mechanical sensors is representative of an artificially induced neuromuscular response; and wherein the second processor is operative to determine if the MMG output signal from any one or more of the second plurality of mechanical sensors is representative of an artificially induced neuromuscular response, and to transmit a portion of the one or more MMG output signals only if it is determined that the MMG output signal from any one or more of the second plurality of mechanical sensors is representative of an artificially induced neuromuscular response.

Clause 21: The system of any of clauses 18-20, wherein the first sensing device is a sensing device according to any of clauses 1-17.

Clause 22: The system of any of clauses 18-21, wherein the second sending device is a sensing device according to any of clauses 1-17.

The invention claimed is:

1. A sensing device, comprising:

a carrier material for placing on a single limb of a patient, one or more alignment indicia disposed on the carrier material for orientation of the carrier material relative to the limb of the patient;

a plurality of neuromuscular sensors disposed on the carrier material, wherein each sensor generates a mechanomyography (MMG) output signal, and wherein each sensor is associated with a different muscle group of the limb; and a processor configured to:

receive a MMG output signal from each of the sensors;

buffer a portion of each MMG output signal;

determine whether any of the buffered MMG output signals is associated with an artificially induced neuromuscular response; and if an artificially induced neuromuscular response is determined, send only those buffered MMG output signals associated with the artificially induced neuromuscular response;

wherein the processor is further configured to periodically send a connection diagnostic data packet, wherein the data packet is a low-footprint, nominal transmission that is performed solely to evaluate whether the connection is still active and/or whether a fidelity of the connection is sufficient to convey data.

2. The sensing device of claim 1, wherein the processor is further configured to indicate that a nerve associated with the affected muscle group has been depolarized.

3. The sensing device of claim 1, wherein the processor is further configured to indicate that a single artificially induced neuromuscular response has been determined.

4. The sensing device of claim 3, wherein the processor is further configured to send an alert.

5. The sensing device of claim 1, wherein the processor is further configured to indicate that more than one artificially induced neuromuscular response has been determined.

6. The sensing device of claim 5, wherein the processor is further configured to send an alert.

7. The sensing device of claim 1, wherein the processor is further configured to, if no artificially induced neuromuscular response is determined:

reduce a representation quality of each of the buffered MMG output signals, wherein the reduced representation quality has at least one of a lower resolution or a lower sampling rate; and send the reduced quality representations of the buffered MMG output signals.

8. The sensing device of claim 1, wherein the processor is further configured to periodically receive a connection diagnostic packet.

9. The sensing device of claim 8, wherein the processor is further configured to generate an alert if the connection diagnostic packet is not received at a periodic interval.

10. The sensing device of claim 1, wherein the processor is further configured to store the MMG output signal from each of the sensors at predetermined intervals.

11. The sensing device of claim 1, wherein the processor is further configured to determine that an electrical stimulus has been applied to the patient; and then store the MMG output signal from each of the sensors.

12. A system, comprising:

a display and/or a speaker;

a stimulator; and a sensing device, comprising:

a carrier material for placing on a single limb of a patient;

a plurality of neuromuscular sensors disposed on the carrier material, wherein each sensor generates a mechanomyography (MMG) output signal, and wherein each sensor is associated with a different muscle group of the limb; and a processor configured to:

receive a MMG output signal from each of the sensors; and determine whether any of the MMG output signals is associated with an artificially induced neuromuscular response, and, if so, send only those MMG output signals associated with artificially induced neuromuscular response;

wherein, if a single artificially induced neuromuscular response has been determined, the display displays a first color and/or the speaker plays a first tone;

wherein, if more than one artificially induced neuromuscular response has been determined, the display displays a second color and/or the speaker plays a second tone;

wherein the first color is different from the second color and the first tone is different from the second tone; and wherein the processor is further configured to periodically send a connection diagnostic data packet, wherein the data packet is a low-footprint, nominal transmission that is performed solely to evaluate whether the connection is still active and/or whether a fidelity of the connection is sufficient to convey data.

13. The system of claim 12, wherein the processor is further configured to receive an indication that an electrical stimulus has been administered to the patient.

14. The system of claim 13, wherein the processor is further configured to store a portion of the MMG output signal from each of the sensors after the electrical stimulus has been administered to the patient.

15. The system of claim 12, wherein the processor is further configured to determine that an electrical stimulus has been administered to the patient.

16. The system of claim 12, wherein the processor is further configured to filter out portions of the MMG output signals that are attributable to gross translation of the limb or gross rotation of the limb before determining whether any of the MMG output signals is associated with an artificially induced neuromuscular response.

17. A sensing device, comprising:

a carrier material for placing on a single limb of a patient;

one or more alignment indicia disposed on the carrier material for orientation of the carrier material relative to the limb of the patient;

a plurality of neuromuscular sensors disposed on the carrier material, wherein each sensor generates a mechanomyography (MMG) output signal, and wherein each sensor is associated with a different muscle group of the limb; and a processor configured to:

receive a MMG output signal from each of the sensors;

only send a subset of the MMG output signals, wherein the subset of the MMG output signals are those associated with an artificially induced neuromuscular response; and periodically send a connection diagnostic data packet, wherein the data packet is a low-footprint, nominal transmission that is performed solely to evaluate whether the connection is still active and/or whether a fidelity of the connection is sufficient to convey data.

18. The sensing device of claim 17, wherein the subset of the MMG output signals are MMG output signals from more than one sensor.

19. The sensing device of claim 17, wherein the processor is configured to examine one or more characteristics of the MMG output signal from each of the sensors using a supervised learning algorithm to determine whether the MMG output signal is representative of an artificially-induced mechanical response.

* * * * *